United States Patent
Ryba

(10) Patent No.: US 7,357,797 B2
(45) Date of Patent: Apr. 15, 2008

(54) SYSTEM AND METHOD FOR VARYING RETURN PRESSURE TO CONTROL TIP TEMPERATURE OF A CRYOABLATION CATHETER

(75) Inventor: Eric Ryba, San Bruno, CA (US)

(73) Assignee: Cryocor, Inc., San Diego, CA (US)

( * ) Notice: Subject to any disclaimer, the term of this patent is extended or adjusted under 35 U.S.C. 154(b) by 106 days.

(21) Appl. No.: 10/881,086

(22) Filed: Jun. 30, 2004

(65) Prior Publication Data

US 2006/0004350 A1    Jan. 5, 2006

(51) Int. Cl.
    *A61B 18/18*    (2006.01)
(52) U.S. Cl. .......................... 606/21; 606/23
(58) Field of Classification Search .......... 606/20–26
    See application file for complete search history.

(56) References Cited

U.S. PATENT DOCUMENTS

| | | | |
|---|---|---|---|
| 3,605,725 A | 9/1971 | Bentov | |
| 3,613,689 A * | 10/1971 | Crump et al. ................. | 606/23 |
| 3,696,813 A | 10/1972 | Wallach | |
| 3,913,581 A * | 10/1975 | Ritson et al. ................. | 606/23 |
| 4,018,227 A | 4/1977 | Wallach | |
| 4,456,017 A | 6/1984 | Miles | |
| 4,586,923 A | 5/1986 | Gould et al. | |
| 4,813,434 A | 3/1989 | Buchbinder et al. | |
| 4,815,478 A | 3/1989 | Buchbinder et al. | |
| 4,886,067 A | 12/1989 | Palermo | |
| 4,960,134 A | 10/1990 | Webster, Jr. | |
| 4,960,411 A | 10/1990 | Buchbinder | |
| 4,976,688 A | 12/1990 | Rosenblum | |
| 5,037,391 A | 8/1991 | Hammerslag et al. | |
| 5,042,985 A | 8/1991 | Elliott et al. | |
| 5,108,368 A | 4/1992 | Hammerslag et al. | |
| 5,114,414 A | 5/1992 | Buchbinder | |
| 5,125,895 A | 6/1992 | Buchbinder et al. | |
| 5,139,496 A | 8/1992 | Hed | |
| 5,190,050 A | 3/1993 | Nitzsche | |
| 5,242,441 A | 9/1993 | Avitall | |
| 5,281,213 A | 1/1994 | Milder et al. | |
| 5,281,215 A | 1/1994 | Milder | |
| 5,318,525 A | 6/1994 | West et al. | |
| 5,322,064 A | 6/1994 | Lundquist | |
| 5,330,466 A | 7/1994 | Imran | |
| 5,334,145 A | 8/1994 | Lundquist et al. | |
| 5,368,564 A | 11/1994 | Savage | |
| 5,423,807 A * | 6/1995 | Milder ........................ | 606/20 |

(Continued)

Primary Examiner—Michael Peffley
(74) Attorney, Agent, or Firm—Nydegger & Associates

(57) ABSTRACT

A cryoablation device having a temperature control system includes an elongated catheter tube that has a central lumen and is formed with a closed distal tip. The distal end of a refrigerant supply line is positioned in the central lumen and distanced from the catheter tube's distal tip to establish an expansion chamber therebetween. A return line, which can be established between the supply line and the catheter tube, is provided to exhaust expanded refrigerant from the chamber. The temperature control system includes a valve that is positioned at a predetermined location along the return line. The valve is adjustable to vary a pressure within the return line to control the operational temperature at the distal tip of the catheter tube. Specifically, the valve can be used to reduce the pressure in the return line to thereby increase the tip temperature, and vice versa.

20 Claims, 2 Drawing Sheets

U.S. PATENT DOCUMENTS

| | | | |
|---|---|---|---|
| 5,507,725 A | 4/1996 | Savage et al. | |
| 5,656,030 A | 8/1997 | Hunjan et al. | |
| 5,715,817 A | 2/1998 | Stevens-Wright et al. | |
| 5,759,182 A * | 6/1998 | Varney et al. | 606/21 |
| 5,876,399 A | 3/1999 | Chja et al. | |
| 5,899,898 A | 5/1999 | Arless et al. | |
| 5,899,899 A | 5/1999 | Arless et al. | |
| 5,906,590 A | 5/1999 | Hunjan et al. | |
| 5,928,191 A | 7/1999 | Houser et al. | |
| 5,944,689 A | 8/1999 | Houser et al. | |
| 5,992,158 A * | 11/1999 | Goddard et al. | 62/51.2 |
| 6,013,052 A | 1/2000 | Durman et al. | |
| 6,024,740 A | 2/2000 | Lesh et al. | |
| 6,048,919 A | 4/2000 | McCullough | |
| 6,066,125 A | 5/2000 | Webster, Jr. | |
| 6,106,518 A | 8/2000 | Wittenberger et al. | |
| 6,117,101 A | 9/2000 | Diederich et al. | |
| 6,123,699 A | 9/2000 | Webster, Jr. | |
| 6,139,544 A | 10/2000 | Mikus et al. | |
| 6,171,277 B1 | 1/2001 | Ponzi | |
| 6,183,435 B1 | 2/2001 | Bumbalough et al. | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,235,019 B1 | 5/2001 | Lehmann et al. | |
| 6,251,105 B1 | 6/2001 | Mikus et al. | |
| 6,254,568 B1 | 7/2001 | Ponzi | |
| 6,267,746 B1 | 7/2001 | Bumbalough | |
| 6,280,439 B1 | 8/2001 | Martin et al. | |
| 6,283,959 B1 * | 9/2001 | Lalonde et al. | 606/21 |
| 6,319,248 B1 | 11/2001 | Nohon | |
| 6,332,880 B1 | 12/2001 | Yang et al. | |
| 6,346,099 B1 | 2/2002 | Altman | |
| 6,383,180 B1 | 5/2002 | Lalonde et al. | |
| 6,407,149 B1 | 6/2002 | McCullough | |
| 6,413,234 B1 | 7/2002 | Thompson et al. | |
| 6,440,126 B1 | 8/2002 | Abboud et al. | |
| 6,468,260 B1 | 10/2002 | Bumbalough et al. | |
| 6,468,268 B1 * | 10/2002 | Abboud et al. | 606/20 |
| 6,471,693 B1 | 10/2002 | Carroll et al. | |
| 6,485,455 B1 | 11/2002 | Thompson et al. | |
| 6,500,167 B1 | 12/2002 | Webster, Jr. | |
| 6,522,933 B2 | 2/2003 | Nguyen | |
| 6,527,769 B2 | 3/2003 | Langberg et al. | |
| 6,540,725 B1 | 4/2003 | Ponzi | |
| 6,540,740 B2 | 4/2003 | Lehmann et al. | |
| 6,547,785 B1 * | 4/2003 | Heiner et al. | 606/21 |
| 6,551,271 B2 | 4/2003 | Nguyen | |
| 6,562,030 B1 | 5/2003 | Abboud et al. | |
| 6,569,114 B2 | 5/2003 | Ponzi et al. | |
| 6,569,158 B1 | 5/2003 | Abboud et al. | |
| 6,571,131 B1 | 5/2003 | Nguyen | |
| 6,575,966 B2 | 6/2003 | Lane et al. | |
| 6,579,278 B1 | 6/2003 | Bencini | |
| 6,579,287 B2 | 6/2003 | Wittenberger et al. | |
| 6,585,717 B1 | 7/2003 | Wittenberger et al. | |
| 6,585,718 B2 | 7/2003 | Hayzelden et al. | |
| 6,585,728 B2 | 7/2003 | Heiner et al. | |
| 6,585,729 B1 | 7/2003 | Eum | |
| 6,589,234 B2 | 7/2003 | Lalonde et al. | |
| 6,592,577 B2 | 7/2003 | Abboud et al. | |
| 6,602,278 B1 | 8/2003 | Thompson et al. | |
| 6,605,086 B2 | 8/2003 | Hayzelden et al. | |
| 6,605,087 B2 | 8/2003 | Swartz et al. | |
| 6,607,505 B1 | 8/2003 | Thompson et al. | |
| 6,610,058 B2 | 8/2003 | Flores | |
| 6,635,053 B1 | 10/2003 | Lalonde et al. | |
| 6,733,494 B2 | 5/2004 | Abboud et al. | |
| 6,755,823 B2 | 6/2004 | Lalonde | |
| 6,761,714 B2 | 7/2004 | Abboud et al. | |
| 6,991,630 B2 * | 1/2006 | Ryba | 606/20 |
| 2001/0021847 A1 * | 9/2001 | Abboud et al. | 606/21 |
| 2001/0025075 A1 | 9/2001 | Smith et al. | |
| 2002/0025998 A1 | 2/2002 | McCullough et al. | |
| 2002/0062122 A1 | 5/2002 | Lehmann et al. | |
| 2002/0111612 A1 | 8/2002 | Lalonde et al. | |
| 2002/0115989 A1 | 8/2002 | Abboud et al. | |
| 2003/0004504 A1 | 1/2003 | Abboud et al. | |
| 2003/0009160 A1 | 1/2003 | Carroll et al. | |
| 2003/0018326 A1 | 1/2003 | Abboud et al. | |
| 2003/0097124 A1 | 5/2003 | Lehmann et al. | |
| 2004/0049178 A1 | 3/2004 | Abboud et al. | |
| 2004/0054361 A1 | 3/2004 | Lehmann et al. | |

\* cited by examiner

SYSTEM AND METHOD FOR VARYING RETURN PRESSURE TO CONTROL TIP TEMPERATURE OF A CRYOABLATION CATHETER

FIELD OF THE INVENTION

The present invention pertains generally to systems and methods for cryoablating internal tissue. More particularly, the present invention pertains to devices and methods for controlling the tip temperature of a cryoablation catheter during a cryoablation procedure. The present invention is particularly, but not exclusively, useful for obtaining a pre-selected cryoablation catheter tip temperature by controlling the "back pressure" in a return line leading from a refrigerant expansion chamber.

BACKGROUND OF THE INVENTION

As the word itself implies, "cryoablation" involves the ablation of tissue (i.e. tissue necrosis or destruction) using extremely low (i.e. cryogenic) temperatures. Typically, cryoablation requires lowering the temperature of the tissue to below approximately minus twenty degrees Centigrade (−20° C.). However, more efficient ablation procedures often call for temperatures as low as minus eighty eight degrees Centigrade (−88° C.) or lower.

In some cases, cell survivability depends not only on the cryoablation temperature, but also the rate at which the cells are cooled to the cryoablation temperature and the rate at which the cooled cells are subsequently warmed. Thus, it is often desirable to control both the cooling and warming rates in a cryoablation procedure. This control, in turn, requires that the temperature of an operative contact surface in the cryoablation device be controlled over a selected temperature range. Another instance in which it is desirable to control the temperature of a cryoablation tip or contact surface occurs when it is necessary to cryoablate tissue to a specific thickness (i.e. at a pre-selected depth from the contact surface). In such a case, it is important to control both the tip temperature and contact time to control the ablation depth.

It is often desirable to cryoablate internal tissue in a relatively non-invasive procedure. For this purpose, cryocatheters have been developed, such as the cryocatheter and associated refrigeration system that is disclosed in co-pending U.S. patent application Ser. No. 10/243,997, entitled "A Refrigeration Source for a Cryoablation Catheter." Co-pending U.S. application Ser. No. 10/243,997 was filed on Sep. 12, 2002, is assigned to the same assignee as the present invention, and is hereby incorporated by reference herein. In one exemplary application of a cryocatheter, conduction blocks can be created in the tissue that are particularly effective for curing heart arrhythmias, such as atrial fibrillation.

In a typical cryocatheter procedure, the distal portion (i.e. cryotip) of the catheter is positioned near or in contact with the tissue requiring ablation (i.e. the target tissue). Next, the cryotip is cooled to a cryogenic temperature to thereby cool and ablate the target tissue. Typically, this is accomplished by expanding a fluid refrigerant into an expansion chamber near the catheter tip and exhausting the expanded refrigerant from the chamber through a return line. For this expansion, the pressure of the refrigerant as it enters the chamber, as well as the pressure in the return line (back pressure), will affect the temperature of the cryotip and the instantaneous cooling power of the cryocatheter. In addition, for a cryoablation system in which the refrigerant undergoes a phase change during expansion (i.e. transitions from a liquid to a gaseous state), the back pressure effects the actual refrigerant boiling temperature. This boiling temperature, in turn, controls the temperature of the cryoablation catheter tip.

In light of the above, it is an object of the present invention to provide systems and methods for controlling the tip temperature of a cryoablation catheter. It is another object of the present invention to provide a temperature control system for a cryoablation device that can either stabilize the cryoablation tip at a constant tip temperature or vary the temperature of the cryoablation tip in accordance with a predetermined schedule. Yet another object of the present invention is to provide a temperature control system for a cryoablation device which is easy to use, relatively simple to implement, and comparatively cost effective.

SUMMARY OF THE INVENTION

The present invention is directed to a cryoablation device having a temperature control system. For the present invention, the device includes an elongated catheter tube that has a central lumen and is formed with a closed distal tip. The device further includes a refrigerant supply unit that is connected to the proximal end of a supply line. The other end of the supply line (i.e. the distal end) is positioned in the central lumen of the catheter tube and distanced from the distal tip. With this cooperation of structure, an expansion chamber is established in the central lumen between the distal end of the supply tube and the closed distal tip of the catheter tube.

In a typical embodiment, the supply line includes a supply tube and a capillary tube, with the capillary tube attached to the distal end of the supply tube. With this combination, the refrigerant supply unit can be activated to introduce a regulated flow of refrigerant into the supply tube for subsequent flow through the capillary tube. From the capillary tube, the refrigerant expands into the expansion chamber absorbing heat as it expands. For the present invention, the device also includes a return line to exhaust expanded refrigerant from the expansion chamber. In a typical embodiment, the return line is established between the supply line and catheter tube. For example, the return line can be established between the inner surface of the catheter tube and the outer surface of the supply line (e.g. the outer surfaces of the supply tube and capillary tube).

For the present invention, the temperature control system of the cryoablation device includes a valve that is positioned at a predetermined location along the return line. Typically, the valve is positioned along the return line to remain at an extracorporeal location throughout a cryoablation procedure. For the temperature control system, the valve is adjustable to vary a pressure within the return line to control the operational temperature at the distal tip of the catheter tube. Specifically, as detailed further below, the valve can be used to vary the pressure in the return line to thereby increase or decrease the tip temperature.

In one aspect of the present invention, the temperature control system includes a control unit and a sensor for measuring a temperature at the distal tip of the catheter tube. For the system, the control unit is configured to compare the measured temperature at the distal tip with a pre-selected temperature and create an error signal. The control unit is connected to the valve, allowing the control unit to adjust the valve until the error signal is a nullity. The result is that the pre-selected temperature is obtained at the distal tip of the catheter tube. With this cooperation of structure, the control unit can be programmed to maintain a pre-selected temperature or vary the tip temperature in accordance with a predetermined schedule.

In a particular embodiment of the device, a fluid refrigerant is used that transitions from a liquid state to a gaseous state as it expands into the expansion chamber. Heat absorbed by the refrigerant during this phase transition (i.e. latent heat) cools the distal tip of the catheter tube and an operative surface that is placed in contact with tissue to be cryoablated. More specifically, for the phase change refrigerant, the boiling point ($T_{boiling}$) of the refrigerant will be a function of the pressure in the expansion chamber where the refrigerant boils. As a consequence, the valve can be used to vary the pressure in the expansion chamber, which in turn, varies the temperature at which the refrigerant boils. For a typical refrigerant, such as nitrous oxide, this effect is more pronounced at lower pressures. Stated another way, at low pressures, a relatively small change in pressure results in a relatively large change in boiling temperature. Thus, in one aspect of the present invention, the device is operated at relatively low expansion chamber pressures (e.g. pressures less than 10 atmospheres) to allow the tip temperature to be controlled using relatively small pressure variations.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
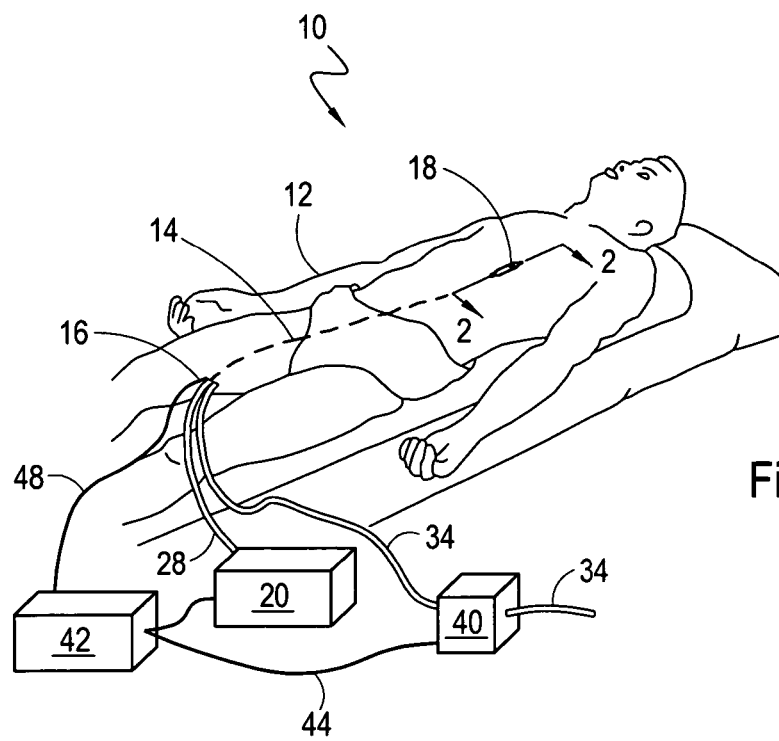
FIG. 1 is a simplified, perspective view of a device for cryoablating tissue at an internal treatment site.

Referring initially to FIG. 1, a cryoablation device 10 for ablating internal target tissue of a patient 12 is shown. As shown, the cryoablation device 10 includes a catheter 14 having a proximal portion 16 that remains outside the patient's body during the procedure and a distal portion 18 that can be inserted into a vasculature. From FIG. 1 it can be seen that the distal portion 18 of the catheter 14 has been inserted into the vasculature of patient 12 through an artery or vein such as the femoral artery, and then advanced through the patient's vasculature until the distal portion 18 is positioned in the upper body of the patient 12. FIG. 1 further shows that the cryoablation device 10 includes a fluid refrigerant supply unit 20 that is positioned to remain at an extracorporeal location throughout the cryoablation procedure.

Figure 2:
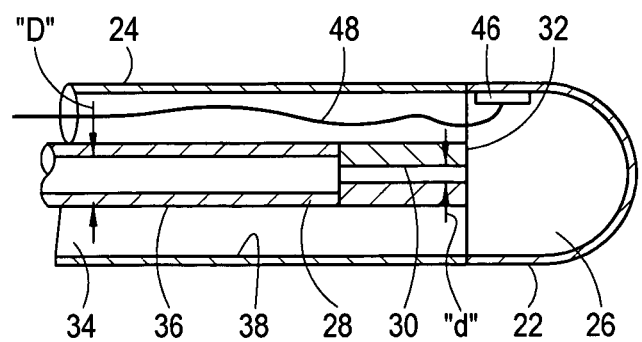
FIG. 2 is a cross-sectional view of the distal end of the device shown in FIG. 1 as seen along 2-2 in FIG. 1.

Referring now to FIG. 2, the distal end of the catheter 14 is shown in greater detail. As shown, the catheter 14 includes a tip member 22 that is attached to the distal end of a catheter tube 24. As further shown, the tip member 22 is formed with an expansion chamber 26. For the cryoablation device 10, the tip member 22 is made of a thermally conductive material such as a metal. A supply line is provided having a supply tube 28 formed with a lumen having a lumen diameter, D, and a capillary tube 30 formed with a lumen having a lumen diameter, d, with D>d. The capillary tube 30 is provided to restrict the flow of refrigerant. FIG. 1 shows that the proximal end of the supply tube 28 is connected to the refrigerant supply unit 20.

As shown in FIG. 2, the capillary tube 30 is attached to the distal end of the supply tube 28 and extends therefrom to a distal end 32. FIG. 2 also shows that both the supply tube 28 and capillary tube 30 are arranged to be substantially co-axial with the catheter tube 24; In addition, the distal end 32 of the capillary tube 30 is distanced from the tip member 22, and thus, the expansion chamber 26 is established therebetween. It can also be seen that a refrigerant return line 34 is established between the outer surface 36 of the supply tube 28 and the inner surface 38 of the catheter tube 24.

Referring back to FIG. 1, it can be seen that a valve 40 is positioned at a location along the return line 34. Typically, the valve 40 is positioned along the return line 34 to remain at an extracorporeal location throughout a cryoablation procedure. For the cryoablation device 10, the valve 40 is adjustable to vary the flow through the return line 34, and hence, controls the pressure within the return line 34. From the valve 40, refrigerant can be piped to a collection tank (not shown), piped to a hospital line for subsequent release to the atmosphere (not shown), directly released to the atmosphere, or the refrigerant can be recycled back to the refrigerant supply unit 20.

With the combination of structure described above and shown in FIGS. 1 and 2, the refrigerant supply unit 20 can be activated to introduce a regulated flow of refrigerant into the supply tube 28 for subsequent flow through the capillary tube 30. The refrigerant then outflows from the capillary tube 30 and expands into the expansion chamber 26 absorbing heat as it expands. From the expansion chamber 26, the refrigerant flows through the return line 34 and through the valve 40.

In one embodiment of the cryoablation device 10, a fluid refrigerant is used that transitions from a liquid state to a gaseous state as it expands into the expansion chamber 26. A suitable refrigerant supply unit 20 for delivering a refrigerant in a liquid state to the distal end 32 of a capillary tube 30 for transition to a gaseous state in the expansion chamber 26 is disclosed in co-pending U.S. patent application Ser. No. 10/243,997, entitled "A Refrigeration Source for a Cryoablation Catheter" filed on Sep. 12, 2002, which is assigned to the same assignee as the present invention. Co-pending U.S. application Ser. No. 10/243,997 is incorporated by reference herein. Heat absorbed by the refrigerant during this phase transition (i.e. latent heat) cools the tip member 22 of the catheter 14.

Figure 3:
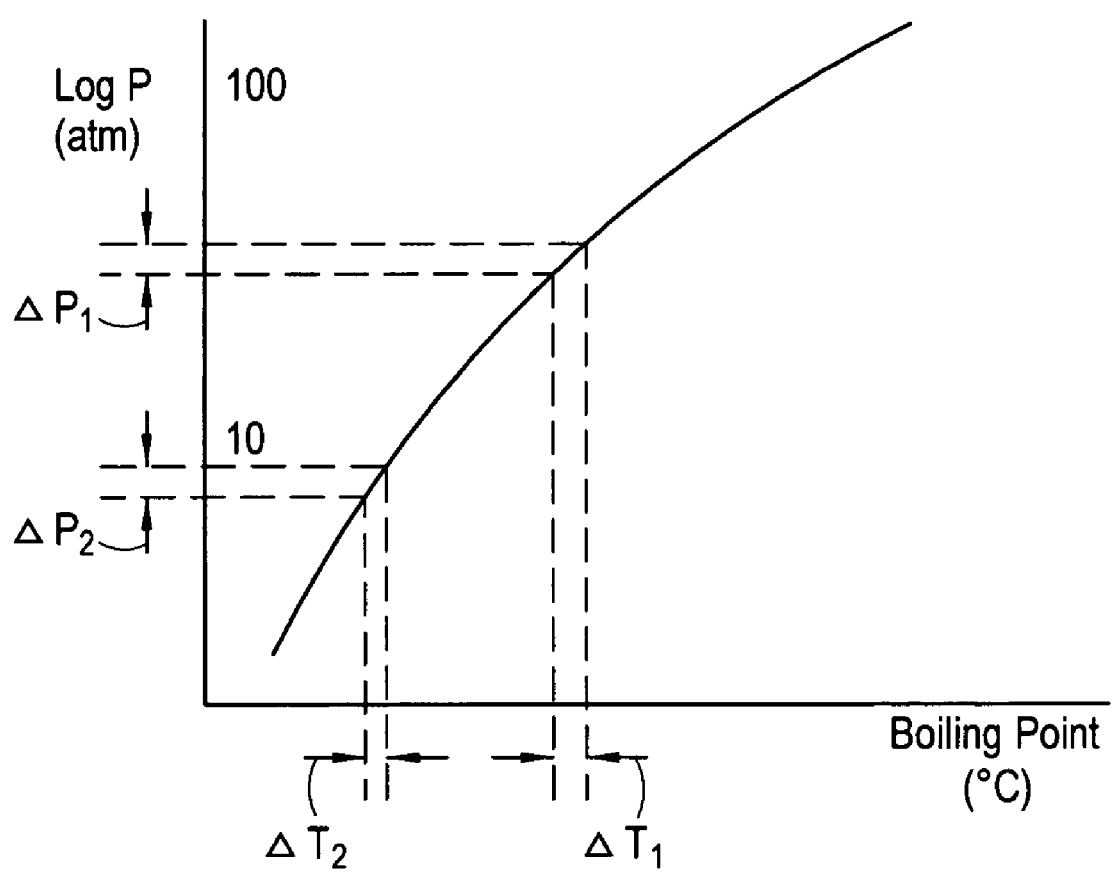
FIG. 3 is a graph showing the relationship between pressure and boiling temperature for an exemplary refrigerant.

Referring now to FIG. 3, it can be seen that for the phase change refrigerant, the boiling point ($T_{boiling}$) of the refrigerant is a function of the pressure, P, where the refrigerant boils. As a consequence of the relationship shown in FIG. 3, the valve 40 (see FIG. 1) can be used to vary the pressure in the expansion chamber 26 (FIG. 2), which in turn, varies the temperature at which the refrigerant boils. For a typical refrigerant, such as nitrous oxide, this effect is more pronounced at lower pressures. Specifically, as shown in FIG. 3, at relatively high pressures (e.g. 20-40 atm), a large change in pressure, $\Delta P_1$ (e.g. $\Delta P_1$=5-10 atm) is required for a relatively small change in boiling temperature, $\Delta T_1$ (e.g. $\Delta T_1$=1-2° C.). On the other hand, as also shown in FIG. 3, at relatively low pressures (e.g. >10 atm), a relatively small change in pressure, $\Delta P_2$ (e.g. $\Delta P_2$=2-3 atm) results in a relatively large change in boiling temperature, $\Delta T_2$ (e.g. $\Delta T_2$=12°-16° C.). Thus, it is possible to operate the cryoablation device 10 at relatively low tip pressures (e.g. <10 atm) to allow the tip temperature to be controlled using relatively small pressure variations. The table presented below gives representative (exemplary) relationships for pressure and temperature over a range of pressures and temperatures.

TABLE

Pressure/Temperature Relationship
(Example for a saturated liquid, e.g. $N_2O$)

| atm | ° C. |
|---|---|
| 1 | −88 |
| 2 | −76 |
| 3 | −68 |
| 4 | −62 |
| 5 | −56.5 |
| 6 | −52 |
| 7 | −48 |
| 8 | −44 |
| 9 | −41.5 |
| 10 | −38.5 |
| 15 | −26.5 |

Referring back to FIG. 1, a more detailed discussion of the temperature control system for the cryoablation device 10 is now presented. As shown in FIG. 1, the valve 40 is positioned along the return line 34 and is adjustable to vary a pressure within the return line 34 to control the operational temperature at the distal tip of the catheter 14. Specifically, the valve 40 can be used, alone or in conjunction with a vacuum pump, to reduce the pressure in the return line 34 to thereby decrease the tip temperature (see FIG. 3), and vice versa. FIG. 1 further shows that the temperature control system includes a control unit 42 that is connected to the valve 40 via wire 44, and accordingly, control signals from the control unit 42 can be used to adjust the valve 40.

Cross-referencing FIG. 1 with FIG. 2, it can be seen that a temperature sensor 46 is positioned in the chamber 26 for measuring a temperature at the distal tip of the catheter 14. As shown, the sensor 46 is connected via wire(s) 48 to the control unit 42. In one embodiment of the system 10, the control unit 42 can include a processor that is programmed to compare the measured temperature at the distal tip with a pre-selected temperature and create an error signal in response. The control unit 42 then sends one or more control signals to the valve 40 to adjust pressure in the chamber 26 until the error signal is a nullity. The result is that the pre-selected temperature is obtained at the distal tip of the catheter 14. For the system 10, the control unit 42 can be programmed to maintain a pre-selected temperature or vary the tip temperature in accordance with a predetermined schedule.

While the particular System And Method For Varying Return Pressure To Control Tip Temperature Of A Cryoablation Catheter as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A cryoablation device having a temperature control system, said device comprising:
   a refrigerant supply unit;
   an elongated catheter tube having a central lumen and formed with a closed distal tip;
   a supply line having a proximal end connected to said refrigerant supply unit and a distal end disposed in the central lumen of said catheter tube and distanced from the distal tip thereof;
   a flow restrictor positioned at the distal end of said supply line to bound an expansion chamber between said flow restrictor and the closed distal tip of said catheter tube, with said flow restrictor delivering a refrigerant from said refrigerant supply unit to the expansion chamber for expansion therein;
   a return line in fluid communication with the expansion chamber for exhausting refrigerant from the expansion chamber, with said return line having a first end bounding the expansion chamber and a second end, wherein said return line defines an unobstructed path between the first end and the second end; and
   a valve positioned at the second end of the return line, said valve being adjustable to vary a pressure in the return line to control a temperature at the distal tip of the catheter tube; wherein said valve is positioned at an extracorporeal location during a cryoablation procedure to establish an unrestricted flow between the flow restrictor and the extracorporeal valve.

2. A device as recited in claim 1 further comprising a means for measuring a temperature at the distal tip of the catheter tube.

3. A device as recited in claim 2 wherein said measuring means comprises a sensor positioned in the expansion chamber.

4. A device as recited in claim 2 further comprising a control unit for adjusting said valve in response to a measured temperature at the distal tip to obtain a pre-selected temperature at the distal tip.

5. A device as recited in claim 4 wherein said control unit further comprises:
   a means for comparing the measured temperature with a reference temperature to create an error signal; and
   a means for adjusting said valve to make the error signal a nullity.

6. A device as recited in claim 5 wherein the reference temperature is equal to the pre-selected temperature.

7. A device as recited in claim 1 wherein said catheter tube has an inner surface, said supply line has an outer surface and the return line is established between the inner surface of said catheter tube and the outer surface of said supply line.

8. A device as recited in claim 1 wherein said supply line comprises a supply tube, said flow restrictor comprises a capillary tube, said supply tube is formed with a lumen having a lumen diameter, D, and said capillary tube is formed with a lumen having a lumen diameter, d, with D>d.

9. A device as recited in claim 1 wherein said supply line and said catheter tube are arranged co-axially.

10. A system for controlling a temperature at a distal tip of a cryoablation catheter, said catheter having a supply line extending to a distal end located within the cryoablation catheter for delivering a refrigerant to an expansion chamber at the distal tip for expansion therein, said system comprising:
    a return line being in fluid communication with the expansion chamber for exhausting expanded refrigerant from the expansion chamber, with said return line having a first end bounding the expansion chamber and a second end, wherein said return line defines an unobstructed path between the first end and the second end;

a flow restrictor positioned at the distal end of said supply line to regulate flow of the refrigerant, with said flow restrictor bounding the expansion chamber;

an adjustable valve at the second end of the return line for varying a pressure in the return line, with said valve being positioned at an extracorporeal location during a cryoablation procedure to establish an unrestricted flow between the flow restrictor and the extracorporeal valve;

a means for measuring a temperature at the distal tip of said cryoablation catheter; and a control unit for comparing the measured temperature with a pre-selected temperature to create an error signal and for adjusting said valve to make the error signal a nullity to obtain the pre-selected temperature at the distal tip of said cryoablation catheter.

11. A system as recited in claim 10 wherein said measuring means comprises a sensor positioned in the expansion chamber.

12. A system as recited in claim 10 wherein the flow restrictor is a capillary tube.

13. A method for cryoablating tissue at a treatment site in the vasculature of a patient, said method comprising the steps of:

providing an elongated catheter tube having a central lumen and formed with a closed distal tip;

establishing a flow restrictor at the distal end of a supply line;

placing the supply line in the central lumen of said catheter tube to position said flow restrictor at a distance from the distal tip thereof to establish an expansion chamber between the flow restrictor and a return line, with said flow restrictor bounding the expansion chamber, and with said return line having a first end bounding the expansion chamber and a second end, wherein said return line defines an unobstructed path between the first end and the second end;

positioning a valve at the second end of the return line, with said valve being positioned at an extracorporeal location during the method to establish an unrestricted flow between the flow restrictor and the extracorporeal valve;

advancing the distal tip of said catheter tube through the patient's vasculature to the treatment site;

introducing a refrigerant into said supply line for outflow from the flow restrictor and expansion in the expansion chamber; and adjusting said valve to reduce a pressure in the return line to decrease a temperature at the distal tip of said catheter tube and, alternatively, to increase the pressure in the return line to increase the temperature at the distal tip of said catheter tube.

14. A method as recited in claim 13 further comprising the step of measuring a temperature at the distal tip of said catheter tube.

15. A method as recited in claim 14 wherein said measuring step is accomplished using a sensor positioned in the expansion chamber.

16. A method as recited in claim 14 further comprising the steps of:

comparing the measured temperature with a reference temperature to create an error signal; and adjusting said valve to make the error signal a nullity.

17. A method as recited in claim 13 wherein said catheter tube has an inner surface, said supply line has an outer surface and the return line is established between the inner surface of said catheter tube and the outer surface of said supply line.

18. A method as recited in claim 13 wherein said supply line comprises a supply tube, said flow restrictor comprises a capillary tube, said supply tube is formed with a lumen having a lumen diameter, D, and said capillary tube is formed with a lumen having a lumen diameter, d, with D>d.

19. A method as recited in claim 13 wherein said supply line and said catheter tube are arranged co-axially.

20. A method as recited in claim 13 wherein said valve adjusting step varies a pressure in the return line to control a temperature at the distal tip of said catheter tube in accordance with a predetermined schedule.

* * * * *